United States Patent [19]

Cohen

[11] 4,128,499

[45] Dec. 5, 1978

[54] LEWIS ACID-FLUORINE COMPOUNDS OF CARBON

[75] Inventor: A. David Cohen, Sarnia, Canada

[73] Assignee: Imperial Oil Limited, Toronto, Canada

[21] Appl. No.: 725,417

[22] Filed: Sep. 22, 1976

Related U.S. Application Data

[63] Continuation-in-part of Ser. No. 523,026, Nov. 12, 1974, abandoned.

[51] Int. Cl.$^2$ .............................................. B01J 27/12
[52] U.S. Cl. ................................. 252/378 R; 252/433; 252/437; 252/439; 252/441; 252/301.1 R
[58] Field of Search .................... 252/301.1 R, 378 R, 252/433, 437, 439, 441; 423/448

[56] References Cited

U.S. PATENT DOCUMENTS

| 2,734,801 | 2/1956 | Brooks | 423/293 |
| 2,903,433 | 9/1959 | Moehl | 252/433 |
| 3,389,964 | 6/1968 | Olstowski | 252/378 R |
| 3,885,007 | 5/1975 | Olsen et al. | 264/2 |
| 3,962,133 | 6/1976 | Rodewald | 252/443 |
| 3,984,352 | 10/1976 | Rodewald | 252/441 |

OTHER PUBLICATIONS

Croft, R., "Graphite Compound," *Research Science and Its Application in Industry*, Jan. 1957, pp. 23-28.
Hooley, J. G., "Isotherms of Metal Chloride Vapors on Graphite," *Carbon*, 1973, vol. 11, pp. 225-236.
Chemical Abstracts, vol. 80, Abstract No. 77807c, 1974.

*Primary Examiner*—Benjamin R. Padgett
*Assistant Examiner*—Deborah L. Kyle
*Attorney, Agent, or Firm*—Joseph J. Dvorak

[57] ABSTRACT

Novel fluoride salts of carbon are prepared by contacting carbon with elemental fluorine and certain Lewis acids. These salts can be used in forming exfoliated graphite and isomerization catalysts.

17 Claims, No Drawings

LEWIS ACID-FLUORINE COMPOUNDS OF CARBON

CROSS REFERENCE TO RELATED APPLICATION

This application is a continuation-in-part of application Ser. No. 523,026, filed Nov. 12, 1974, now abandoned.

BACKGROUND OF THE INVENTION

1. Field of the Invention

The present invention relates to novel Lewis acid fluorine compounds of carbon and their method of preparation.

2. Prior Art

As is well known, carbon exists in a number of different allotropic forms. Of particular interest from a chemical point of view is the highly crystalline form of carbon known as graphite and the amorphous forms of carbon, such as charcoal and lampblack. Because of the differences in allotropy, the amorphous and crystalline forms of carbon do not have completely analogous chemical reactivity. Thus, for example, graphite forms intercalation compounds with a wide variety of materials. These inclusion or intercalation compounds have been described as being heteropolar because of their ionic character. See, for example, *Angew. Chem. Internat Edit.*, Vol. 2, No. 2, p. 67-73 (1963). Indeed, graphite has been shown to form blue graphite salts with sulfates and nitrates. In particular, the nitrate salt of graphite, $[3HNO_3-]C_{24}^+$, has been shown to have a conductivity which approaches that of copper. See, *Proc. Roy. Soc. Lond.*, A325, p. 437 (1971). Graphite also has been reported to form intercalation compounds with hydrogen fluoride, see, for example, *Russian J. of Inorg. Chem.*, 17, p. 632 (1972), and with hydrogen fluoride and chlorine trifluoride, see, for example, *Russian J. Inorg. Chem.*, 17, p. 1366 (1972).

In U.S. Pat. No. 3,844,837, lamellar graphite compounds, such as the tetrafluoroborate salt of graphite, are described. These compounds were prepared by impressing an electric current between an anode and a graphite cathode immersed in a nonagueous salt solution such as a nonaqueous solution of lithium tetrafluoroborate. In any event, the electrochemical intercalation suggested by the patent disclosure does not lead to fully intercalated materials of graphite, commonly referred to as "first stage compounds."

SUMMARY OF THE INVENTION

It has now been found that carbon salts can be formed from carbon, elemental fluorine and a Lewis acid. Thus, one embodiment of the present invention is concerned with novel composition of matter comprising carbon, fluorine and a Lewis acid.

This invention also includes a method of preparing such novel compositions.

The novel compositions of the present invention are useful, for example, as an isomerization catalyst for paraffins and in the formation of exfoliated graphite, to mention just a few uses.

DETAILED DESCRIPTION OF THE INVENTION

As has already been mentioned, the present invention is based on the discovery of novel compounds of carbon with Lewis acids and elemental fluorine. Thus, graphite and amorphous carbon are allowed to react with Lewis acids and elemental fluorine at temperatures generally ranging as low as $-127°$ C. to temperatures ranging as high as $625°$ C. and preferably at temperatures of from about $-78.5°$ C. to about $300°$ C.

The graphite and amorphous carbon employed in forming the novel compounds can be employed in any desired form. It can be finely divided material, fibers or woven cloth. The form in which the carbon material will take will depend, of course, to a large extent on the desired end use of the resulting carbon compound.

In any event, the carbon material is contacted with elemental fluorine and a Lewis acid at temperatures ranging generally in the range of about $-127°$ C. to about $625°$ C. The precise temperature, of course, will depend upon the thermal stability of the resultant product. Also, as will be appreciated, at temperatures above about $625°$ C. elemental fluorine will burn carbonaceous material thereby forming fluorocarbons, the formation of which can be troublesome. Thus, it is preferable to contact the carbon material with elemental fluorine and Lewis acid at temperatures of from $-78.5°$ C. to $300°$ C. Generally the contacting is most conveniently carried out near atmospheric pressure; however, pressures ranging from 0.05 to 100 atmospheres may be employed.

In view of the reactivity of elemental fluorine, it is particularly preferred to keep the partial pressure of elemental fluorine in contact with the carbon sufficiently low so as to completely avoid, or at least minimize, any burning of the carbon to low molecular weight fluorocarbons such as $CF_4$. Thus, the fluorine can be diluted with inert gases such as helium, argon, nitrogen, carbon tetrafluoride or the like, and mixtures of the foregoing. If the Lewis acid employed has a sufficiently high vapor pressure at the reaction temperature selected, the Lewis acid can be used, in effect as a diluent, to keep the partial pressure of elemental fluorine in contact with the carbon relatively low. On the other hand, when the Lewis acid is employed in the liquid state, it is advantageous to use higher fluorine pressures to ensure reasonable reaction rates.

The Lewis acids employed in the practice of the present invention typically are materials which are fluid, i.e. gases or liquids, at reaction temperatures and preferably are materials that are gases or volatile liquids at ambient temperatures. Among the Lewis acids employed in the practice of the present invention are $SO_3$, $BF_3$, $PF_5$, $TaF_5$, $AsF_5$, $PtF_4$, $SbF_5$, $SiF_4$, $NbF_5$, $UF_6$, $TiF_4$ and $VF_5$.

Typically, the mole ratio of Lewis acid to fluorine will be in the range of about 100 to 0.05 and preferably in the range of 10 to 0.1. The inert gas-Lewis acid-fluorine mole ratio would be 10:1:1.

The carbon material is reacted with the Lewis acid and fluorine for a time sifficient to permit complete conversion of the carbon material to the novel carbon compounds. Typically, the conversion is completed in as little as 2 hours. Reaction is observed visually by a change in color of the carbon from gray to blue.

Since the resultant products of the present invention tend to be heteropolar, or salt-like, they can be thought of as Lewis acid fluoride salts. Alternatively, they can be thought of as superacid salts of carbon. Indeed, these compounds optionally can be represented by the general formula $C_n^+X^-$ where X is a fluoroanion of a Lewis acid. For example, $X^-$ is $SO_3F^-$, $BF_4^-$, $PF_6^-$, $TaF_6^-$, $AsF_6^-$, $PtF_5^-$, $SbF_6^-$, $SiF_5^-$, $NbF_6^-$, $UF_7^-$, $TiF_5^-$ and $VF_6^-$. Typically, n will be a number between 6 and 24.

In any event, as little as 0.05 wt. % of the guest anion can be introduced in or reacted with the carbon and graphite structure and as much as about 75 wt. % and higher of the guest anion can be combined with the carbon. Preferably from about 20 wt. % to about 45 wt. % of the guest anion is introduced into or reacted or combined with the graphite or amorphous carbon structure.

Most typically, the weight ratio of anion to carbon cation is in the range of about 1:28 to about 1:6.

These superacid salts can be thermally decomposed with concomitant formation of exfoliated graphite. Thus, exfoliated graphite can be prepared by first contacting graphite with fluorine and one of the foregoing Lewis acids and thereafter heating the so-treated graphite at temperatures sufficient to promote the loss of the Lewis acid, thereby exfoliating the graphite. In the case when $BF_3$ is the Lewis acid, for example, the $BF_3/F_2$ treated graphite is heated rapidly to about 800° C. resulting in the formation of exfoliated graphite.

The following examples are provided to more completely illustrate the invention.

EXAMPLE 1

In this example a 10–20 mesh Madagascar plate graphite obtained from The Asbury Graphite Mills, Inc., New Jersey, was employed. The amount of graphite used in each run was 5 grams and the sample was treated at 1 atmosphere pressure at 50° C. for 7 hours in a polytetrafluoroethylene tube. The test conditions and results are given in the table below.

Table I

| Run No. | Gas Used | Flow Rate, NTP, cc/min. | Wt. % Material Gain | Formed |
|---|---|---|---|---|
| 1 | $F_2$ | 120 | 0.0 | Graphite unchanged |
| 2 | $BF_3$ | 10 | 0.0 | Graphite unchanged |
| 3 | $BF_3$ $F_2$ | 10 120 | 41.4% | $C_n^+[BF_4^-]$ |

EXAMPLE 2

In this example so-called "superacid salts of carbon and graphite" were prepared under ambient conditions. The graphite material employed was the same as that used in Example 1. The amorphous carbon was an activated coconut charcoal obtained from Fisher Scientific Company which had a particle size ranging from 6 to 14 mesh and a surface area of about 1500 m²/g. The carbon was treated in the polytetrafluoroethylene tube with the Lewis acid and fluorine at the flow rate of about 30 cc/minute. The ratio of helium to Lewis acid to fluorine was about 10:1.5:1.5. The resultant superacid salts were dull blue colored solids. The test results are given in Table II below:

Table II

| Run No. | Carbon Material | Lewis Acid | Wt. % Guest Anion | Superacid Salt |
|---|---|---|---|---|
| 1 | Graphite | $BF_3$ | 24 | $[BF_4^-]C_n^+$ |
| 2 | Graphite | $PF_5$ | 32 | $[PF_6^-]C_n^+$ |
| 3 | Charcoal | $BF_3$ | 30 | $[BF_4^-]C_n^+$ |

EXAMPLE 3

Following the procedure of Example 1, a number of runs were made with a charge of approximately 5 grams of graphite in a quartz tube. The graphite was contacted at room temperature with a $F_2/BF_3$ gas stream diluted with $N_2$. The metallic gray graphite turned to a dull blue color. The results of these runs are given in Table III below:

Table III

| Run No. | Amount of Graphite, gms | % Increase in weight |
|---|---|---|
| 42 | 5.0 | 41.9 |
| 44 | 4.6 | 31.3 |
| 46 | 5.0 | 40.5 |
| 48 | 5.0 | 41.9 |

EXAMPLE 4

X-ray powder diffraction patterns were obtained on the products of Example 3 and on untreated graphite using $Co_k$ radiation. The strongest peak observed in the pattern of graphite is due to planes having a spacing of 3.29 Å. This diffraction maximum is not present in any of the products of Example 3 which indicates that unreacted graphite is not present in the product samples. The results are summarized in Table IV below:

Table IV
(Measurements in Angstroms)

| | Sample | | | |
|---|---|---|---|---|
| Graphite | Run No. 42 | Run No. 44 | Run No. 46 | Run No. 48 |
| | 10.3(w) | 10.2(s) | 10.5(m) | 11.4(m) |
| | 6.2(w) | | 6.3(w) | 6.6(s) |
| 3.61(m) | 3.58(vs) | 3.60(vs) | 3.56(vs) | 3.82(vs) |
| 3.29(vs) | | | | |
| 1.66(s) | 2.75(w) | 2.71(m) | 2.75(w) | |
| | | | | 2.25(w) | w = weak
m = medium
s = strong
vs = very strong

EXAMPLE 5

A comparison of infrared spectrum in KBr pellets over the range of 4000 cm$^{-1}$ to 400 cm$^{-1}$ of several of the products of Example 3 with commerically available $LiBF_4$, $C_4F$ and $(CF)_n$ are given in Table V below. It should be noted that all the Example 3 samples have strong absorptions in the region of 1180 cm$^{-1}$ to 1200 cm$^{-1}$, the principal absorption region for $BF_4^-$.

Table V
(Measurements in cm$^{-1}$)

| | | Sample | | | | |
|---|---|---|---|---|---|---|
| $LiBF_4$* | $C_4F$* | $(CF)_n$* | Run No. 44 | | Run No. 46 | |
| 1640 | 1575 | | 1625 ⎫ 1590 ⎭ db | | 1570 | (br) |
| | (w,br) | | | | | |
| 1250 | 1250 (w, br) | 1225 (s, sh) | | | 1250 | (w, br) |
| 1180 ⎫ 1020 ⎭ | vs, br | | 1125 | 1125 (s, tr) | 1125 ⎫ 1085 1030 ⎭ | (s, tr) |
| | | | 1085 1035 ⎭ | | | |

Table V-continued

| (Measurements in $cm^{-1}$) Sample | | | | |
|---|---|---|---|---|
| $LiBF_4$* | $C_4F$* | $(CF)_n$* | Run No. 44 | Run No. 46 |
| 645 | | 670 (w) | | |
| 535 ⎫ db 525 ⎭ | | 450 ⎫ w, br 350 ⎭ | 535 | |

*Purchased from Ozark-Mahoning Co., Tulsa, Okla.
vs = very strong
w = weak
db = doublet
s = strong
br = broad
sh = sharp
tr = triplet

EXAMPLE 6

This example demonstrates the technique of preparing superacid carbon salts from the less volatile Lewis acids. The graphite employed in this example was the same material employed in Example 1 and the amorphous carbon was the same material employed in Example 2. In this example, an equimolar stream of helium and fluorine was passed at a rate of 10 cc/minute over $TaF_5$, heated to 150° C., and this stream containing $TaF_5$ vapor was passed over the carbon substrate also at 150° C. The results are given in the table below:

Table VI

| Run No. | Carbon Material | Lewis Acid | Wt. % Guest Anion | Superacid Salt |
|---|---|---|---|---|
| 1 | Graphite | $TaF_5$ | 29 | $[TaF_6^-]C^+$ |
| 2 | Charcoal | $TaF_5$ | 21 | $[TaF_6^-]C^+$ |

EXAMPLE 7

In this example an exfoliated graphite was prepared by heating the superacid salt $[C_n^+BF_4^-]$ of Example 2 rapidly to about 800° C. This heating caused a rapid loss of $BF_3$ and carbon fluorides and gave a vermicular graphite which had expanded over 800% in volume and whose surface area had increased from 1.5 $m^2/g$ to about 70 $m^2/g$.

EXAMPLE 8

In this example a superacid salt of both $BF_4^-$ and $TaF_6^-$ were prepared using the exfoliated graphite of Example 4 and following the general procedures outlined in Examples 2 and 3. The results are given in Table VII:

Table VII

| Run No. | Carbon Material | Lewis Acid | Wt. % Guest Anion | Superacid Salt |
|---|---|---|---|---|
| 1 | Exfoliated Graphite | $BF_3$ | 44 | $[BF_4^-]C^+$ |
| 2 | Exfoliated Graphite | $TaF_5$ | 75 | $[TaF_6^-]C^+$ |

EXAMPLE 9

This example demonstrates the ability to form superacid salts of fibers with the same physical form as the original fiber. Thus, a graphite fiber known as grade WCA graphite cloth sold by Union Carbide and having a surface area of 5 $m^2/g$ was treated with an equimolar mixture of $BF_3$, fluorine and helium under ambient conditions at a flow rate of 45 cc/minute for 2 hours and the resultant fiber showed a gain of 27 wt. %.

EXAMPLE 10

This example demonstrates the utility of the superacid salts as isomerization catalysts. In this particular example, a superacid salt, $[BF_4^-]C^+$, was prepared in accordance with the procedure of Example 2 using graphite as the carbon material. A stainless steel bomb was charged with about 2 cc of catalyst in a nitrogen atmosphere. The catalyst was pretreated with n-butene by simply flushing the cell with this vapor at ambient conditions. Thereafter the bomb was flushed with n-butane at ambient temperature and pressured and sealed. Approximately 2 cc of n-butane at NTP was sealed in a bomb and the bomb was heated at a temperature of about 120° C. for 0.5 hours. Thereafter, the gas was analyzed by gas chromatography and found it contained an isobutane to normal butane ratio of 1:1.

Various modifications can be made in the present invention without departing from the spirit of the scope thereof.

What is claimed is:

1. A composition of matter consisting essentially of carbon containing in combination therewith fluorine and a Lewis acid selected from the group consisting of $BF_3$, $PF_5$, $AsF_5$, $SbF_5$, $TaF_5$, $SiF_4$, $SO_3$, $PtF_4$, $NbF_5$, $VF_5$, $UF_6$ and $TiF_4$, said composition being in the form of the solid.

2. The composition of claim 1 wherein the Lewis acid is $BF_3$.

3. The composition of claim 1 wherein the Lewis acid is $PF_5$.

4. The composition of claim 1 wherein a Lewis acid is $TaF_5$.

5. The composition of claim 1 wherein the Lewis acid is $SO_3$.

6. The composition of claim 1 wherein the amount of fluorine and Lewis acid combined with carbon ranges from about 0.05 wt. % to about 75 wt. %.

7. A process for preparing a composition of matter containing carbon and in combinaton therewith fluorine and a Lewis acid comprising: contacting carbon with a Lewis acid selected from the group consisting of $BF_3$, $PF_5$, $AsF_5$, $SbF_5$, $TaF_5$, $SiF_4$, $SO_3$, $PtF_4$, $NbF_5$, $VF_5$, $UF_6$ and $TiF_4$ and fluorine at a temperature at which the Lewis acid is at least partially fluid for a time sufficient to combine from about 0.05 wt. % to about 75 wt. % of said fluorine and said Lewis acid with said carbon thereby forming a composition of matter containing carbon and in combination therewith fluorine and a Lewis acid.

8. The process of claim 7 wherein the carbon contacted is amorphous.

9. The process of claim 7 wherein the carbon is graphitic.

10. The process of claim 7 wherein the fluorine and Lewis acid are diluted with an inert gas.

11. The process of claim 7 wherein the temperatures are in the range of −127° to 625° C.

12. The process of claim 11 wherein the Lewis acid is $BF_3$.

13. A process for forming exfoliated graphite comprising contacting graphite with fluorine and a Lewis acid selected from the group consisting of $BF_3$, $PF_5$, $AsF_5$, $SbF_5$, $TaF_5$, $SiF_4$, $SO_3$, $PtF_4$, $NbF_5$, $VF_5$, $UF_6$ and $TiF_4$ for a time sufficient to form a solid composition of matter comprising carbon containing in combination therewith said fluorine and said Lewis acid and thereafter heating the so treated graphite at elevated temperatures so as to decompose the treated graphite thereby exfoliating it.

14. The process of claim 13 wherein the Lewis acid is $BF_3$ and the treated graphite is heated to about 800° C.

15. The composition of claim 1 wherein the amount of fluorine and Lewis acid combined with carbon ranges from about 20 wt. % to about 45 wt. %.

16. A composition of matter containing fluorine and a Lewis acid together in combination with graphite in the form a solid, said fluorine and said Lewis acid being present in said composition in the range of from about 20 wt. % to about 45 wt. %, said Lewis acid being selected from the group consisting of $BF_3$, $PF_5$, $AsF_5$, $SbF_5$, $TaF_5$, $SiF_4$, $SO_3$, $PtF_4$, $NbF_5$, $VF_5$, $UF_6$ and $TiF_4$.

17. A composition of matter consisting essentially of carbon having in combination therewith a fluoroanion of a Lewis acid, said composition being a solid and having the general formula $$C_n^+ X^-$$

wherein $C^+$ is carbon;

$X^-$ is a fluoroanion selected from the group consisting of $SO_3F^-$, $BF_4^-$, $PF_6^-$, $TaF_6^-$, $AsF_6^-$, $PtF_5^-$, $SbF_5^-$, $NbF_6^-$, $UF_7^-$, $TiF_5^-$ and $VF_6^-$; and n is an integer between 6 and 24.

* * * * *